US011253230B2

(12) United States Patent
Iwama et al.

(10) Patent No.: US 11,253,230 B2
(45) Date of Patent: Feb. 22, 2022

(54) ULTRASOUND DIAGNOSIS APPARATUS AND IMAGE PROCESSING METHOD

(71) Applicant: Toshiba Medical Systems Corporation, Otawara (JP)

(72) Inventors: Nobuyuki Iwama, Nasushiobara (JP); Hironobu Hongou, Otawara (JP); Isao Uchiumi, Nasushiobara (JP); Koichi Morikawa, Nasushiobara (JP); Yasuo Miyajima, Utsunomiya (JP); Takatoshi Okumura, Yaita (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 729 days.

(21) Appl. No.: 14/690,023

(22) Filed: Apr. 17, 2015

(65) Prior Publication Data
US 2015/0216508 A1   Aug. 6, 2015

Related U.S. Application Data

(63) Continuation-in-part of application No. PCT/JP2013/078387, filed on Oct. 18, 2013.

(30) Foreign Application Priority Data

Oct. 19, 2012 (JP) .............................. JP2012-232019
Oct. 18, 2013 (JP) .............................. JP2013-217854

(51) Int. Cl.
*A61B 8/08* (2006.01)
*A61B 8/00* (2006.01)
(Continued)

(52) U.S. Cl.
CPC ............ *A61B 8/485* (2013.01); *A61B 8/4461* (2013.01); *A61B 8/463* (2013.01); *A61B 8/465* (2013.01);
(Continued)

(58) Field of Classification Search
CPC ....... A61B 8/485; A61B 8/4461; A61B 8/465; A61B 8/481; A61B 8/5207; A61B 8/54;
(Continued)

(56) References Cited

U.S. PATENT DOCUMENTS 4,819,621 A * 4/1989 Ueberle ........... A61B 17/22004
600/437
5,324,422 A * 6/1994 Colleran ................. A61M 1/28
210/143

(Continued)

FOREIGN PATENT DOCUMENTS

JP   10-201760 A   8/1998
JP   11-221217 A   8/1999
(Continued)

OTHER PUBLICATIONS

Klibanov et al., "Ligand-Carrying Gas-Filled Microbubbles: Ultrasound Contrast Agents for Targeted Molecular Imaging" Bioconjugate Chem 2005, vol. 16, No. 1, pp. 9-17.*
(Continued)

*Primary Examiner* — Colin T. Sakamoto
(74) *Attorney, Agent, or Firm* — Oblon, McClelland, Maier & Neustadt, L.L.P.

(57) ABSTRACT

An ultrasound diagnosis apparatus includes a transmitting and receiving circuitry, an input circuitry, and a processing circuitry. The transmitting and receiving circuitry transmits a first ultrasound wave used for changing the shape of a tissue in the body of a patient and transmits/receives a second ultrasound wave that is transmitted/received with timing different from that of the first ultrasound wave. The input circuitry receives an input of a request indicating that the first ultrasound wave should be transmitted. When the input circuitry has received the input of the request indicating that the first ultrasound wave should be transmitted, the processing circuitry controls the transmission of the first
(Continued)

ultrasound wave in accordance with the strength of a reflected-wave signal of the second ultrasound wave or one or more pixel values of an image resulting from an imaging process performed by using the reflected-wave signal of the second ultrasound wave.

8 Claims, 10 Drawing Sheets

(51) Int. Cl.
    *G01S 7/52*     (2006.01)
    *G01S 15/89*     (2006.01)

(52) U.S. Cl.
    CPC .......... *A61B 8/481* (2013.01); *A61B 8/5207* (2013.01); *A61B 8/54* (2013.01); *G01S 7/5205* (2013.01); *G01S 7/52022* (2013.01); *G01S 7/52039* (2013.01); *G01S 7/52042* (2013.01); *G01S 7/52071* (2013.01); *G01S 15/8915* (2013.01); *G01S 15/8979* (2013.01)

(58) Field of Classification Search
    CPC ............ G01S 7/52022; G01S 7/52089; G01S 7/52042; G01S 7/52071; G01S 15/8915; G01S 15/8979
    See application file for complete search history.

(56) References Cited

U.S. PATENT DOCUMENTS

| | | | | |
|---|---|---|---|---|
| 6,508,774 B1* | 1/2003 | Acker | ................ | A61B 8/0833 600/439 |
| 6,537,222 B1* | 3/2003 | Clark | ................ | A61B 8/481 600/458 |
| 2010/0317971 A1* | 12/2010 | Fan | ................ | A61B 8/08 600/439 |
| 2011/0046484 A1* | 2/2011 | Adams | ................ | A61B 8/00 600/440 |
| 2011/0066030 A1 | 3/2011 | Yao | | |
| 2011/0077520 A1 | 3/2011 | Osawa | | |

FOREIGN PATENT DOCUMENTS

| | | |
|---|---|---|
| JP | 2008-188162 A | 8/2008 |
| JP | 2011-72584 A | 4/2011 |
| JP | 2012-100997 A | 5/2012 |

OTHER PUBLICATIONS

Nightingale, "Acoustic Radiation Force Impulse (ARFI) Imaging: a Review" Curr Med Imaging Rev. Nov. 1, 2011; 7(4): 328-339.*

Wrede et al., "Controlled positioning of microbubbles and induced cavitation using a dual-frequency transducer and microfiber adhesion techniques" Ultrasonics Sonochemistry, vol. 43, May 2018, pp. 114-119 (Year: 2018).*

Pallwein et al., "Value of contrast-enhanced ultrasound and elastography in imaging of prostate cancer" Current Opinion in Urology, vol. 17, Issue 1, pp. 39-47, Jan. 2007 (Year: 2007).*

International Search Report dated Dec. 24, 2013 for PCT/JP2013/078387 Filed on Oct. 18, 2013 (English Language).

International Written Opinion dated Dec. 24, 2013 for PCT/JP2013/078387 Filed on Oct. 18, 2013.

* cited by examiner

FIG.2
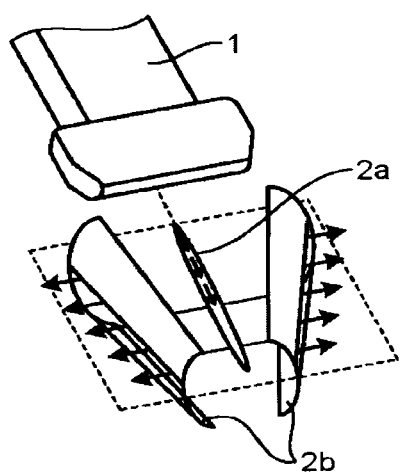
FIG.3
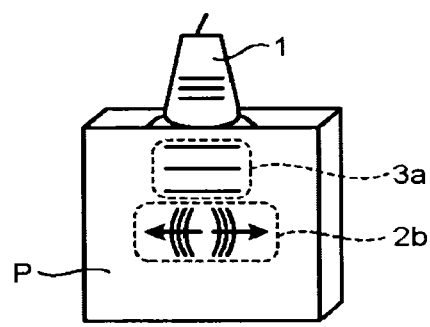
FIG.4
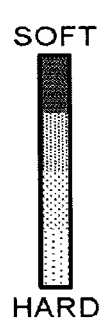
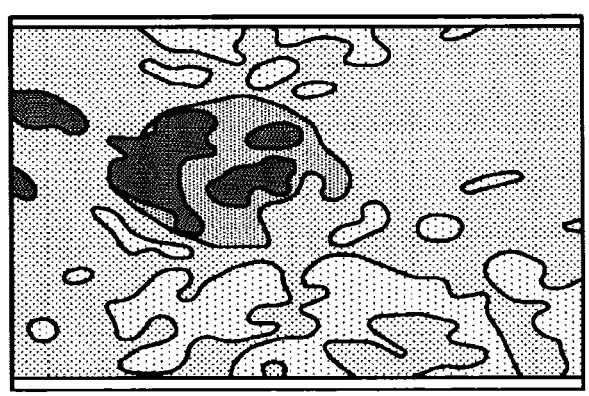

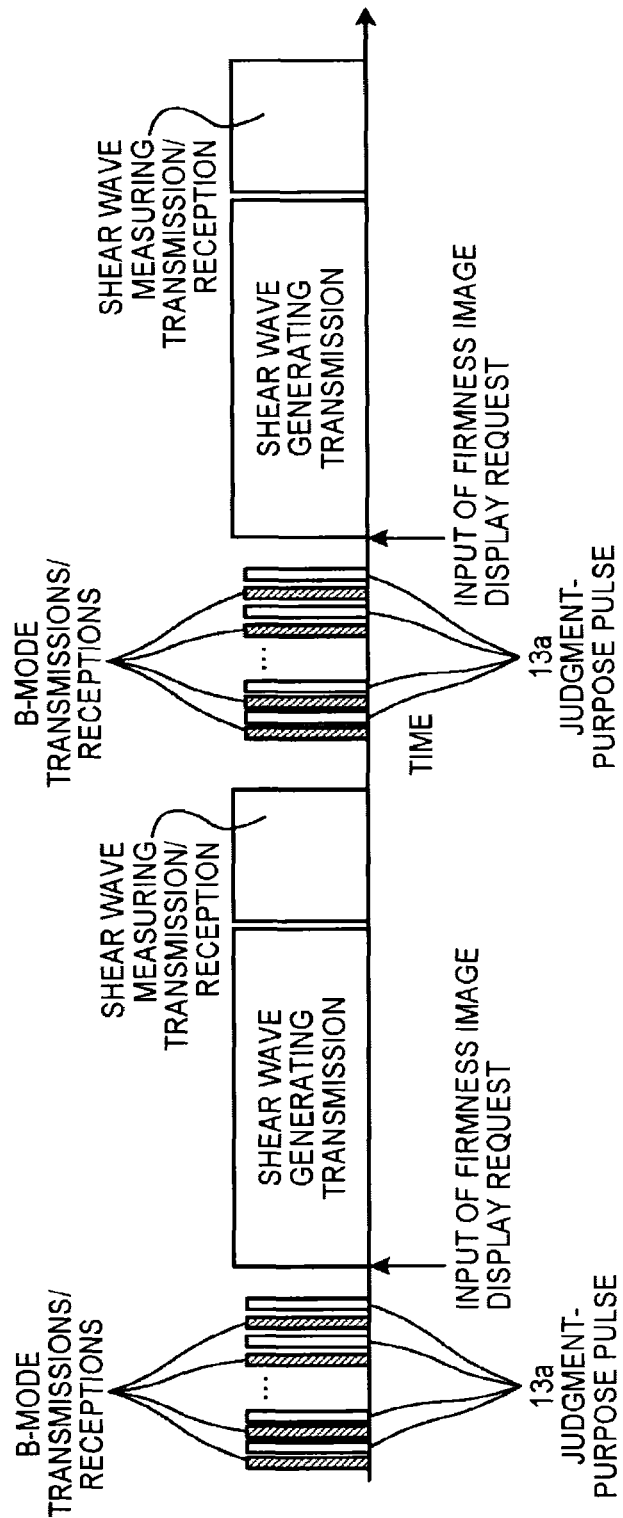

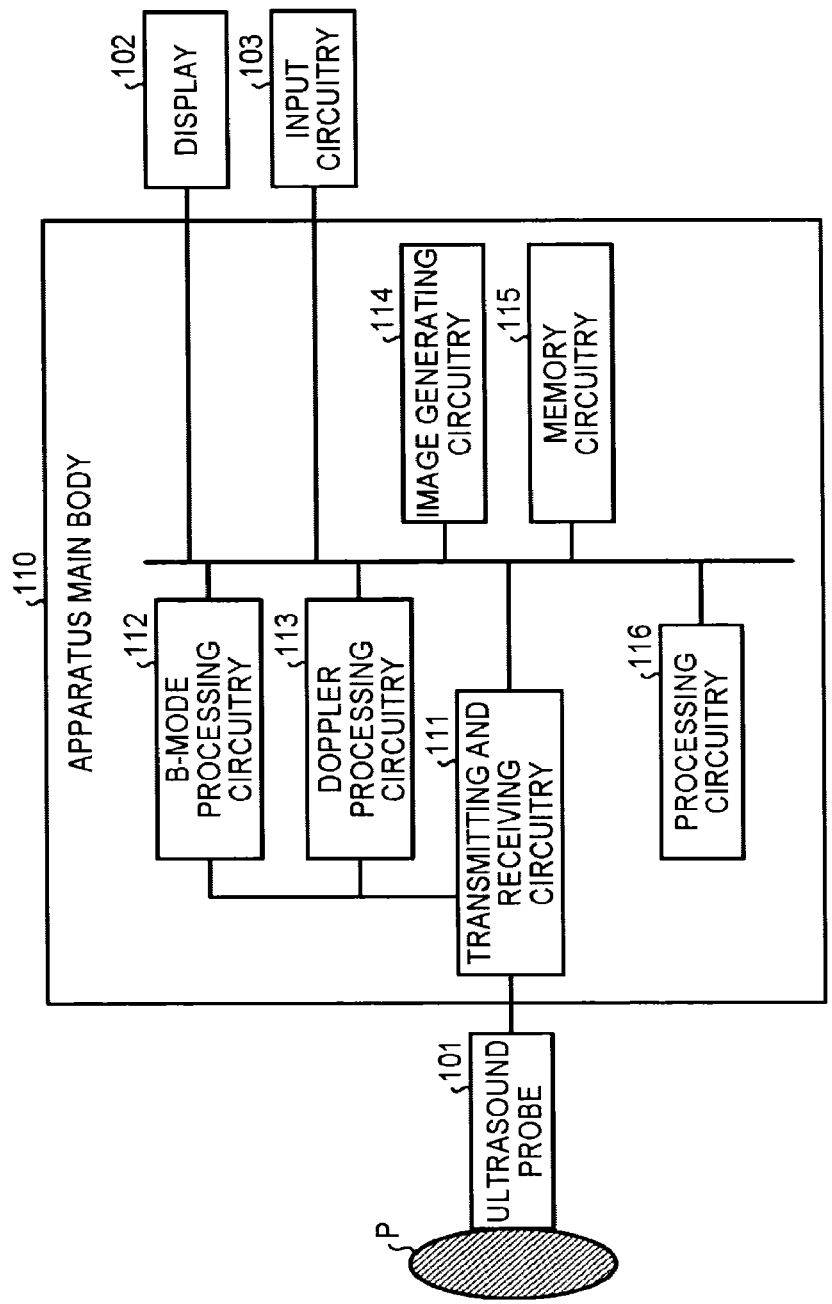

ULTRASOUND DIAGNOSIS APPARATUS AND IMAGE PROCESSING METHOD

CROSS-REFERENCE TO RELATED APPLICATIONS

This application is a continuation-in-part of PCT international application Ser. No. PCT/JP2013/078387 filed on Oct. 18, 2013 which designates the United States, incorporated herein by reference, and which claims the benefit of priority from Japanese Patent Application No. 2012-232019, filed on Oct. 19, 2012, and Japanese Patent Application No. 2013-217854, filed on Oct. 18, 2013, the entire contents of which are incorporated herein by reference.

FIELD

Embodiments described herein relate generally to an ultrasound diagnosis apparatus and an image processing method.

BACKGROUND

Conventionally, elastography is known as a technique for imaging firmness of a tissue in a patient's body. To implement elastography, a method is known by which the firmness of a tissue in a patient's body is evaluated by causing an ultrasound probe to transmit push pulses, which are focused ultrasound pulses each having a high sound pressure, and further measuring the propagation speed of a shear wave generated thereby.

As the push pulses to implement elastography, ultrasound pulses that are more powerful than ultrasound pulses used for B-mode tomography are used, so as to generate the shear wave. More specifically, the ultrasound pulses used for B-mode tomography are, for example, configured so that two waves are emitted at 100 volts [V]. In contrast, the push pulses are, for example, configured so that 1000 waves are emitted three to four times at tens of volts. Because such powerful ultrasound pulses are used as the push pulses, users are required to address a number of issues when using the push pulses.

For example, users are required to address the issue of an increase in the temperature at the surface of the ultrasound probe. More specifically, if a push pulse is transmitted while the ultrasound probe is not in contact with the patient's body, because the acoustic impedance at the surface of the probe is very much different from the acoustic impedance in the air, the energy of the transmitted push pulse is absorbed at the surface of the ultrasound probe, and as a result, the temperature increases as a heat loss. For example, when the temperature at the surface of the ultrasound probe becomes 43 degrees or higher, an impact on tissues in the patient's body is concerned about. Further, an increase in the temperature at the surface may lead to a degradation of ultrasound transducer elements themselves.

In addition, when using a contrast agent, users are also required to address the issue of an impact on tissues in the patient's body that may be made via the contrast agent. More specifically, if microbubbles of the contrast agent burst due to a resonance with the push pulses, it is considered that there is a possibility that an impact is made on tissues in the patient's body that are positioned near the bubbles. In recent years, contrast agents that have a longer remaining period than conventional products have been developed so as to acquire sharper images. Thus, when implementing elastography after using a contrast agent, users are required to address this issue, in particular.

Users are required to address these issues not only when using push pulses in elastography, but also when, for example, using any ultrasound wave that is transmitted for the purpose of changing the shape of a tissue in the body of an examined subject (a patient), such as an ultrasound wave used in a Drug Delivery System (DDS) or an ultrasound wave used for hemostasis.

BRIEF DESCRIPTION OF THE DRAWINGS

FIG. 2 is a first drawing for explaining push pulses and a shear wave;

FIG. 3 is a second drawing for explaining the push pulses and the shear wave;

FIG. 4 is a drawing of an example of firmness image data generated by an image generating unit;

FIG. 13 is a drawing for explaining a modification example of the workflow in the elastography procedure according to the third embodiment; and FIG. 14 is a block diagram of an exemplary configuration of an ultrasound diagnosis apparatus according to other embodiments.

DETAILED DESCRIPTION

An ultrasound diagnosis apparatus includes transmitting and receiving circuitry, input circuitry, and processing circuitry. The transmitting and receiving circuitry transmits a first ultrasound wave used for changing the shape of a tissue in the body of a patient and transmits/receives a second ultrasound wave that is transmitted/received with timing different from that of the first ultrasound wave. The input circuitry receives an input of a request indicating that the first ultrasound wave should be transmitted. When the input circuitry has received the input of the request indicating that the first ultrasound wave should be transmitted, the processing circuitry controls the transmission of the first ultrasound wave in accordance with the strength of a reflected-wave signal of the second ultrasound wave or one or more pixel values of an image resulting from an imaging process performed by using the reflected-wave signal of the second ultrasound wave.

Exemplary embodiments of an ultrasound diagnosis apparatus and an image processing method (hereinafter, "control program") will be explained below, with reference to the accompanying drawings.

First Embodiment

Figure 1:
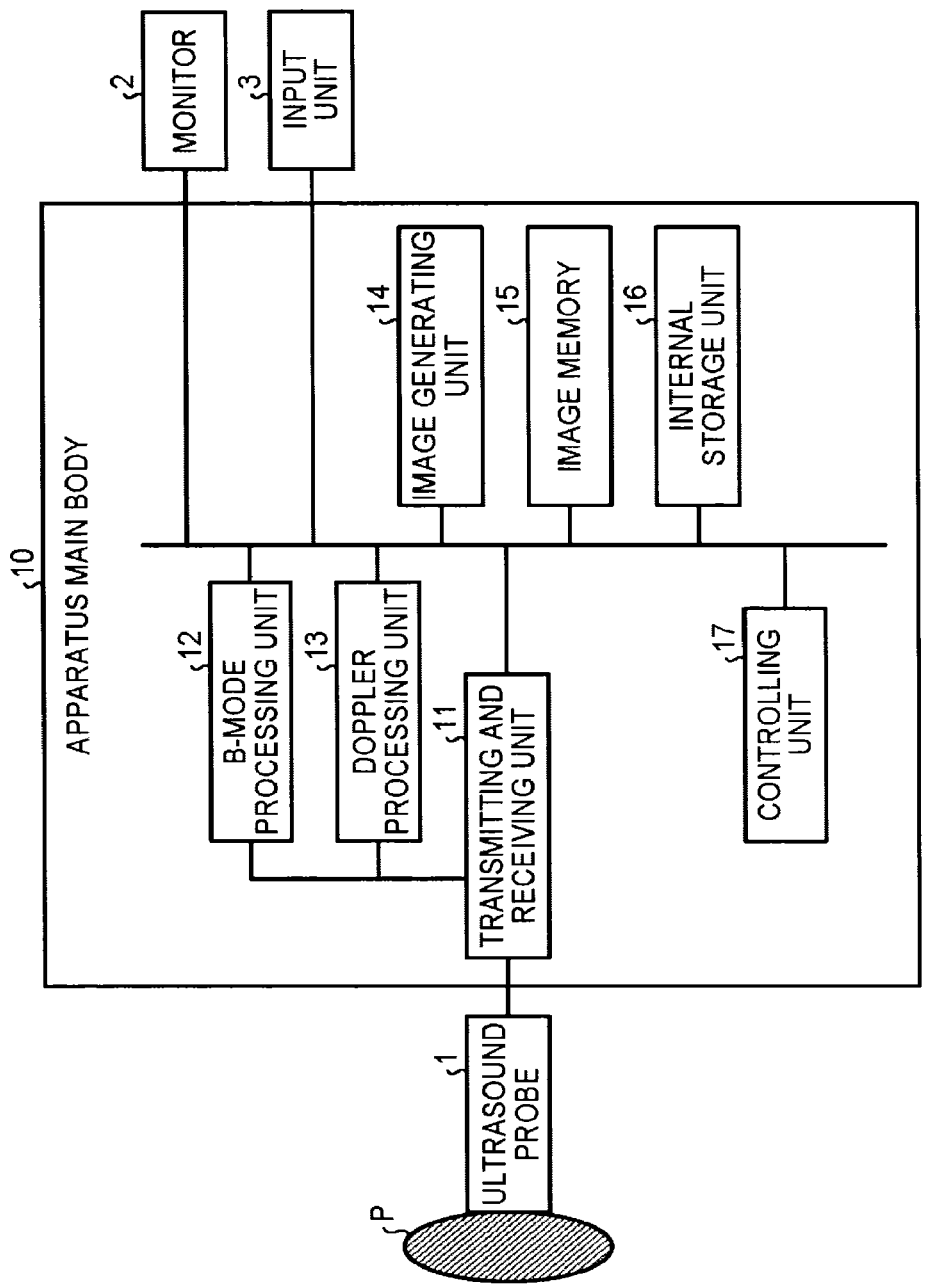
FIG. 1 is a block diagram of an exemplary configuration of an ultrasound diagnosis apparatus according to a first embodiment.

First, a configuration of an ultrasound diagnosis apparatus according to a first embodiment will be explained. FIG. 1 is a block diagram of an exemplary configuration of the ultrasound diagnosis apparatus according to the first embodiment. The ultrasound diagnosis apparatus according to the first embodiment is an apparatus capable of implementing elastography. Elastography is implemented to generate and display an image (hereinafter, a "firmness image") obtained by imaging firmness of a tissue in a patient's body. As shown in FIG. 1, the ultrasound diagnosis apparatus according to the first embodiment includes an ultrasound probe 1, a monitor 2, an input unit 3, and an apparatus main body 10.

The ultrasound probe 1 includes a plurality of transducer elements, which transmit an ultrasound wave based on a drive signal supplied from a transmitting and receiving unit 11 included in the apparatus main body 10 (explained later). The transducer elements included in the ultrasound probe 1 are, for example, piezoelectric transducer elements. The ultrasound probe 1 receives a reflected-wave signal from an examined subject (hereinafter, "patient") P and converts the received reflected-wave signal into an electric signal. Further, the ultrasound probe 1 includes matching layers included in the piezoelectric transducer elements, as well as a backing member that prevents ultrasound waves from propagating rearward from the piezoelectric transducer elements. The ultrasound probe 1 is detachably connected to the apparatus main body 10.

When an ultrasound wave is transmitted from the ultrasound probe 1 to the patient P, the transmitted ultrasound wave is repeatedly reflected on a surface of discontinuity of acoustic impedances at a tissue in the body of the patient P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift, depending on a velocity component of the moving members with respect to the ultrasound wave transmission direction.

The first embodiment is applicable to a situation where the ultrasound probe 1 illustrated in FIG. 1 is a one-dimensional ultrasound probe in which the plurality of piezoelectric transducer elements are arranged in a row, to a situation where the ultrasound probe 1 is a one-dimensional ultrasound probe in which the plurality of piezoelectric transducer elements arranged in a row are mechanically caused to swing, or to a situation where the ultrasound probe 1 is a two-dimensional ultrasound probe in which the plurality of piezoelectric transducer elements are two-dimensionally arranged in a grid formation.

The monitor 2 is a display device configured to display a Graphical User Interface (GUI) used by an operator of the ultrasound diagnosis apparatus to input various types of setting requests through the input unit 3 and to display ultrasound image data and the like generated by the apparatus main body 10.

The input unit 3 is configured to receive inputs of various types of requests from the operator of the ultrasound diagnosis apparatus and to transfer the received various types of requests to the apparatus main body 10. The input unit 3 is configured with a mouse, a keyboard, a button, a panel switch, a touch command screen, a foot switch, a trackball, and the like. For example, the input unit 3 is configured to receive an input of a firmness image display request from the operator and to output the received firmness image display request to a controlling unit 17 (explained later). The firmness image display request is an example of a request indicating that ultrasound waves used for changing the shape of a tissue in the body of a patient should be transmitted.

The apparatus main body 10 is an apparatus configured to generate ultrasound image data based on the reflected-wave signal received by the ultrasound probe 1. As shown in FIG. 1, the apparatus main body 10 includes the transmitting and receiving unit 11, a B-mode processing unit 12, a Doppler processing unit 13, an image generating unit 14, an image memory 15, an internal storage unit 16, and the controlling unit 17.

The transmitting and receiving unit 11 is configured to control ultrasound transmissions and receptions performed by the ultrasound probe 1, on the basis of an instruction from the controlling unit 17 (explained later). The transmitting and receiving unit 11 includes a pulse generator, a transmission delaying unit, a pulser, and the like and supplies the drive signal to the ultrasound probe 1. The pulse generator repeatedly generates a rate pulse for forming a transmission ultrasound wave at a predetermined rate frequency. Further, the transmission delaying unit applies a delay period that is required to converge the ultrasound wave generated by the ultrasound probe 1 into the form of a beam and to determine transmission directionality and that corresponds to each of the piezoelectric transducer elements, to each of the rate pulses generated by the pulse generator. Further, the pulser applies a drive signal (a drive pulse) to the ultrasound probe 1 with timing based on the rate pulses. The transmission delaying unit arbitrarily adjusts the transmission directions of the ultrasound waves transmitted from the piezoelectric transducer element surfaces, by varying the delay periods applied to the rate pulses.

The transmitting and receiving unit 11 has a function to be able to instantly change the transmission frequency, the transmission drive voltage, and the like, for the purpose of executing a predetermined scanning sequence based on an instruction from the controlling unit 17. In particular, the configuration to change the transmission drive voltage is realized by using a linear-amplifier-type transmitting circuit of which the value can be instantly switched or by using a mechanism configured to electrically switch between a plurality of power source voltages and to transmit a rectangular pulse.

The transmitting and receiving unit 11 includes a pre-amplifier, an Analog/Digital (A/D) converter, a reception delaying unit, an adder, and the like and generates reflected-wave data by performing various types of processes on the reflected-wave signal received by the ultrasound probe 1. The pre-amplifier amplifies the reflected-wave signal for each of channels. The A/D converter applies an A/D conversion to the amplified reflected-wave signal. The reception delaying unit applies a delay period required to determine reception directionality to the result of the A/D conversion. The adder performs an adding process on the reflected-wave signals processed by the reception delaying unit so as to generate the reflected-wave data. As a result of the adding process performed by the adder, reflected components from the direction corresponding to the reception directionality of the reflected-wave signals are emphasized. A comprehensive beam used in an ultrasound transmission/reception is thus formed according to the reception directionality and the transmission directionality.

When a two-dimensional scan is performed on the patient P, the transmitting and receiving unit 11 causes the ultrasound probe 1 to transmit two-dimensional ultrasound beams. The transmitting and receiving unit 11 then generates two-dimensional reflected-wave data from the two-dimensional reflected-wave signals received by the ultrasound probe 1. When a three-dimensional scan is performed on the patient P, the transmitting and receiving unit 11 causes the ultrasound probe 1 to transmit three-dimensional ultrasound beams. The transmitting and receiving unit 11 then generates three-dimensional reflected-wave data from the three-dimensional reflected-wave signals received by the ultrasound probe 1.

Output signals from the transmitting and receiving unit 11 can be in a form selected from various forms. For example, the output signals may be in the form of signals called Radio Frequency (RF) signals that contain phase information or may be in the form of amplitude information obtained after an envelope detection process.

Further, when a firmness image display request has been received, the transmitting and receiving unit 11 generates a shear wave by causing the ultrasound probe 1 to transmit push pulses, on the basis of an instruction from the controlling unit 17.

FIGS. 2 and 3 are drawings for explaining push pulses and a shear wave. For example, as illustrated in FIG. 2, the transmitting and receiving unit 11 causes the ultrasound probe 1 to emit ultrasound waves (push pulses) consisting of approximately 1000 waves at tens of volts three to four times, while using one point in a focus position 2a as a focus point. After that, the transmitting and receiving unit 11 generates a shear wave 2b by causing push pulses to be transmitted while moving the focus point to deeper positions along the focus position 2a. Subsequently, as illustrated in FIG. 3, the transmitting and receiving unit 11 causes the ultrasound probe 1 to transmit a shear wave measuring pulse 3a on the basis of an instruction from the controlling unit 17, for the purpose of measuring a propagation speed of the generated shear wave 2b. The push pulses are examples of ultrasound waves that are transmitted for the purpose of changing the shape of a tissue in the body of a patient.

The B-mode processing unit 12 and the Doppler processing unit 13 are signal processing units that are configured to perform various types of signal processing processes on the reflected-wave data generated by the transmitting and receiving unit 11 from the reflected-wave signals. The B-mode processing unit 12 receives the reflected-wave data from the transmitting and receiving unit 11 and generates data (B-mode data) in which the strength of each signal is expressed by a degree of brightness, by performing a logarithmic amplification, an envelope detection process, and the like on the received reflected-wave data. Further, the Doppler processing unit 13 obtains velocity information from the reflected-wave data received from the transmitting and receiving unit 11 by performing a frequency analysis, and further generates data (Doppler data) obtained by extracting moving member information such as a velocity, a dispersion, a power, and the like that are under the influence of the Doppler effect, for a plurality of points. In this situation, the moving member may be, for example, the bloodstream, a tissue such as the cardiac wall, and/or a contrast agent.

When a firmness image display request has been received, the Doppler processing unit 13 generates strain distribution information for displaying the firmness of the tissue in the patient's body in color, on the basis of an instruction from the controlling unit 17. For example, by measuring the propagation speed of the shear wave 2b generated by the push pulses, the Doppler processing unit 13 generates the strain distribution information. More specifically, the Doppler processing unit 13 generates data (tissue Doppler data) obtained by extracting motion information based on the Doppler effect on the tissues that are present in a scanned region, by receiving reflective-wave data of the shear wave measuring pulse 3a from the transmitting and receiving unit 11 and performing a frequency analysis on the received reflected-wave data. Subsequently, the Doppler processing unit 13 calculates a displacement by time-integrating the velocity components of the tissue Doppler data. After that, the Doppler processing unit 13 calculates a local strain of the tissue by performing a predetermined calculation (e.g., spatial differentiation) while using the calculated displacement. Subsequently, the Doppler processing unit 13 generates the strain distribution information by color-coding the values of the calculated local strain of the tissue and mapping the color-coded values in corresponding positions. The firmer a tissue is, the less easily the tissue changes the shape thereof. Accordingly, the strain value of a firmer tissue is smaller, whereas the strain value of a softer tissue in a patient's body is larger. In other words, the strain value indicates the firmness (elasticity) of the tissue. Thus, the shear wave measuring pulse 3a is a tissue-Doppler-purpose transmission pulse. The elasticity described above may be calculated by the B-mode processing unit 12 by detecting a displacement of the tissue between adjacent frames on the basis of a cross-correlation between ultrasound reception Radio Frequency (RF) signal. In that situation, the shear wave measuring pulse 3a is a B-mode-purpose transmission pulse.

The image generating unit 14 is configured to generate ultrasound image data from the data generated by the B-mode processing unit 12 and the Doppler processing unit 13. In other words, from the two-dimensional B-mode data generated by the B-mode processing unit 12, the image generating unit 14 generates two-dimensional B-mode image data in which the strength of the reflected wave is expressed by a degree of brightness. Further, from the two-dimensional Doppler data generated by the Doppler processing unit 13, the image generating unit 14 generates two-dimensional Doppler image data expressing moving member information. The two-dimensional Doppler image data is velocity image data, dispersion image data, power image data, or image data combining these types of image data.

In this situation, generally speaking, the image generating unit 14 converts (by performing a scan convert process) a scanning line signal sequence from an ultrasound scan into a scanning line signal sequence in a video format used by, for example, television and generates display-purpose ultrasound image data. More specifically, the image generating unit 14 generates the display-purpose ultrasound image data by performing a coordinate transformation process compliant with the ultrasound scanning mode used by the ultrasound probe 1. Further, as various types of image processing processes other than the scan convert process, the image generating unit 14 performs, for example, an image processing process (a smoothing process) to re-generate a brightness-average image or an image processing process (an edge enhancement process) using a differential filter within images, while using a plurality of image frames obtained after the scan convert process is performed. Further, the image generating unit 14 synthesizes additional information (text information of various parameters, scale graduations, body marks, and the like) with the ultrasound image data.

In other words, the B-mode data and the Doppler data are the ultrasound image data before the scan convert process is performed. The data generated by the image generating unit 14 is the display-purpose ultrasound image data obtained after the scan convert process is performed. The B-mode data and the Doppler data may also be referred to as raw data.

Further, the image generating unit 14 generates firmness image data in which the firmness of the tissue in the patient's body is displayed in color, from the strain distribution information generated by the Doppler processing unit 13. FIG. 4 is a drawing of an example of the firmness image data generated by the image generating unit 14. As illustrated in FIG. 4, the image generating unit 14 causes the monitor 2 to display an image in which levels of firmness ("soft/hard") of the tissue in the patient's body are expressed in mutually-different colors.

The image memory 15 is a memory for storing therein the display-purpose image data generated by the image generating unit 14. Further, the image memory 15 is also able to store therein the data generated by the B-mode processing unit 12 and the Doppler processing unit 13. After a diagnosis process, for example, the operator is able to invoke the B-mode data or the Doppler data stored in the image memory 15. The invoked data serves as the display-purpose ultrasound image data via the image generating unit 14.

The internal storage unit 16 stores therein various types of data such as a control program to realize ultrasound transmissions and receptions, image processing, and display processing, as well as diagnosis information (e.g., patients' IDs, medical doctors' observations), diagnosis protocols, and various types of body marks. Further, the internal storage unit 16 may be used, as necessary, for storing therein any of the image data stored in the image memory 15. Further, it is possible to transfer the data stored in the internal storage unit 16 to an external apparatus.

The controlling unit 17 is configured to control the entire processes performed by the ultrasound diagnosis apparatus. More specifically, based on the various types of setting requests input by the operator via the input unit 3 and various types of control programs and various types of data read from the internal storage unit 16, the controlling unit 17 controls processes performed by the transmitting and receiving unit 11, the B-mode processing unit 12, the Doppler processing unit 13, and the image generating unit 14. Further, the controlling unit 17 exercises control so that the monitor 2 displays the display-purpose image data stored in the image memory 15 and the internal storage unit 16. Further, the controlling unit 17 exercises control so that the display-purpose image data generated by the image generating unit 14 is stored in the internal storage unit 16 or the like. Further, the controlling unit 17 exercises control so that medical image data received from the operator via the input unit 3 is transferred from an external apparatus 6 to the internal storage unit 16 or to the image generating unit 14, via a network 100 and an interface unit 18.

An overall configuration of the ultrasound diagnosis apparatus according to the first embodiment has thus been explained. The ultrasound diagnosis apparatus according to the first embodiment configured as described above images the firmness of a tissue in a patient's body by implementing elastography.

When elastography is implemented, the ultrasound probe is caused to transmit the push pulses so as to generate the shear wave. Because the push pulses are ultrasound waves that are transmitted for the purpose of changing the shape of a tissue in the body of a patient, users are required to address, for example, the issue of an increase in the temperature at the surface of the ultrasound probe and the issue of an impact on tissues in the patient's body that made be made via a contrast agent, if a contrast agent is being used.

Figure 5:
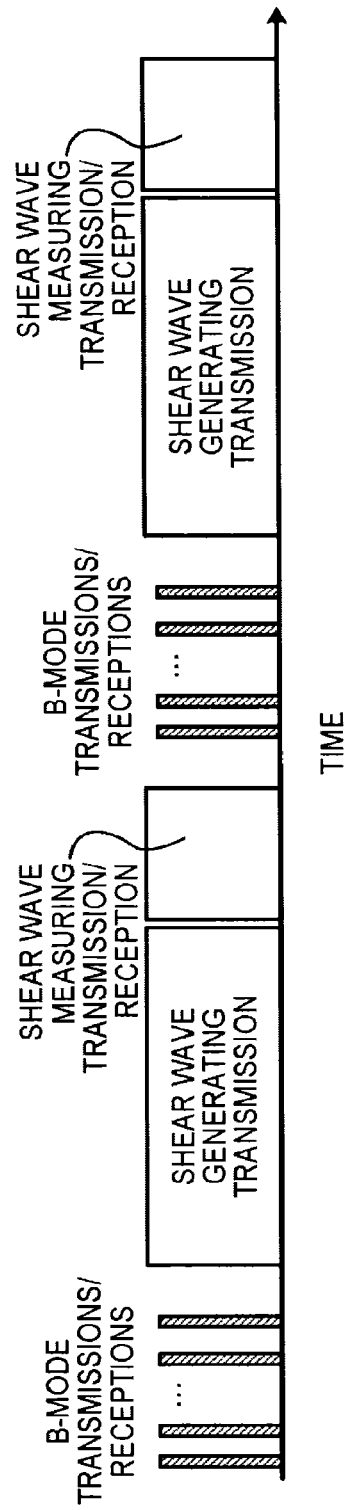
FIG. 5 is a drawing for explaining a workflow in a conventional elastography procedure.

FIG. 5 is a drawing for explaining a workflow (a timing chart) in a conventional elastography procedure. As illustrated in FIG. 5, when implementing elastography by using a shear wave, the operator switches the display mode of an ultrasound diagnosis apparatus into a display mode for elastography (which may be referred to as an "elastography mode" for example). In the elastography mode, a B-mode pulse is repeatedly transmitted/received so that a B-mode image is displayed on the monitor 2 in a substantially real-time manner, except when a process for displaying a firmness image is being performed. The operator operates the ultrasound probe 1 while viewing the displayed B-mode image and makes a firmness image display request when the ultrasound probe 1 is at a position where the operator wishes to have a firmness image thereof displayed (e.g., at a position where a site conjectured to have a tumor is being displayed). In response to the display request, push pulses are transmitted from the ultrasound probe 1, so that the process for displaying a firmness image is started. Subsequently, in the elastography procedure, firmness image data is generated by measuring the propagation speed of the shear wave generated by the push pulses, while using a shear wave measuring pulse. As explained here, the elastography procedure can repeatedly be performed in accordance with the needs of the operator.

In this situation, if the ultrasound probe 1 is positioned away from the patient P, because the acoustic impedance at the surface of the probe is very much different from the acoustic impedance in the air, the energy of the transmitted push pulses are absorbed at the surface of the ultrasound probe, and as a result, the temperature increases as a heat loss.

Further, in an example of a workflow of elastography, contrast harmonic imaging may be used in combination therewith. For example, contrast harmonic imaging is performed after administering a contrast agent to the patient P, so as to estimate a tumor site on the basis of the position of a blood vessel that nourishes the tumor and to subsequently view a firmness image of the vicinity of the estimated tumor site. In that situation, if the contrast agent used in the contrast harmonic imaging procedure remains, there is a possibility that microbubbles of the contrast agent may burst due to a resonance with the push pulses and an impact may be made on tissues in the patient's body that are positioned near the bubbles.

To cope with this situation, the ultrasound diagnosis apparatus according to the first embodiment is configured so that the processes described below are performed by the controlling unit 17, so as to safely use the ultrasound waves transmitted for the purpose of changing the shape of a tissue in the body of the patient.

When the input unit 3 has received a firmness image display request, the controlling unit 17 according to the first embodiment controls the transmission of push pulses in accordance with the strength of reflected-wave signals of B-mode pulses. For example, the controlling unit 17 receives the firmness image display request from the input unit 3. The controlling unit 17 causes the transmitting and receiving unit 11 to transmit B-mode pulses and receives reflected-wave signals of the transmitted B-mode pulses. The B-mode pulses are examples of ultrasound waves used in an imaging process. The B-mode pulses are also examples of ultrasound waves transmitted with timing that is different from that of the push pulses.

By using the strength of the received reflected-wave signals, the controlling unit 17 performs a process of judging whether or not the ultrasound probe 1 is positioned away from (is out of contact with) the patient P, so as to address the issue of an increase in the temperature at the surface of the ultrasound probe. For example, if the strength of the reflected-wave signals in a predetermined first depth range is equal to or higher than a first threshold value, the controlling unit 17 permits push pulses to be transmitted. On the contrary, if the strength of the reflected-wave signals in the predetermined first depth range is lower than the first threshold value, the controlling unit 17 does not permit push pulses to be transmitted.

Figure 6:
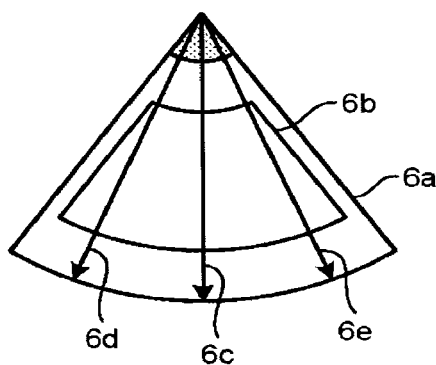
FIG. 6 is a first drawing for explaining a process performed by a controlling unit.
Figure 7:
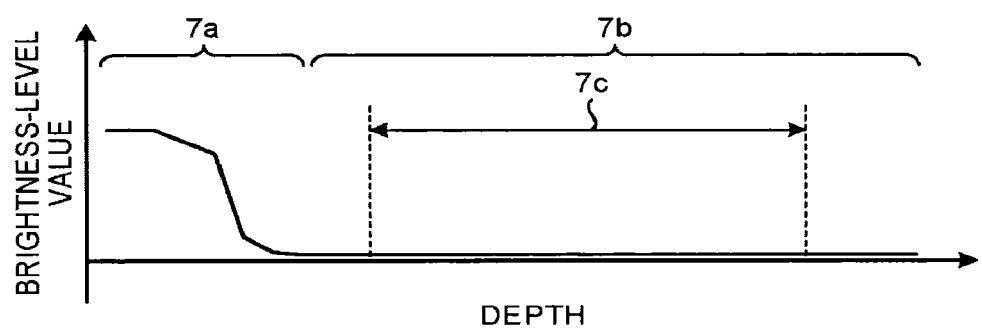
FIG. 7 is a second drawing for explaining the process performed by the controlling unit.

Next, the process performed by the controlling unit 17 to judge whether or not a part or the entirety of the surface of the ultrasound probe 1 is positioned away from the patient P will be explained, with reference to FIGS. 6 and 7. FIGS. 6 and 7 are drawings for explaining a process performed by the controlling unit 17. FIG. 6 illustrates an example of an ultrasound image 6a generated in a B-mode. In the ultrasound image 6a, a region of interest 6b serving as a processing target has been set in advance by the operator of the ultrasound diagnosis apparatus.

FIG. 7 illustrates an example of brightness-level values on a scanning line 6c that passes through the region of interest 6b. In FIG. 7, the vertical axis expresses the brightness-level value (a pixel value) of the ultrasound image 6a, whereas the horizontal axis expresses the depth of the ultrasound image 6a. If the ultrasound probe 1 is positioned away from the patient P, the transmitted ultrasound waves are not emitted from the surface of the ultrasound probe 1 and gradually attenuate while being repeatedly reflected between the lens surface and the transducer elements. For this reason, as illustrated in FIG. 7, a strong reflected-wave signal is received in a range 7a, whereas almost no reflected-wave signal is received in a range 7b so that a white noise level is exhibited. From each of a scanning lines 6d and 6e, brightness-level values are obtained in a manner similar to those from the scanning line 6c. In the present example, the situation where the controlling unit 17 makes the judgment by using the brightness-level values is explained, because the explanation is based on an association between the ultrasound image and the scanning lines; however, it should be noted that the brightness-level values correspond to strengths of the reflected-wave signals. In other words, the controlling unit 17 is able to judge whether or not a part or the entirety of the surface of the ultrasound probe 1 is positioned away from the patient P by using either the strength of the reflected-wave signals or the brightness-level values. When the strength of the reflected-wave signals is being used, the depth direction is expressed by time, and not by the distance.

For example, the controlling unit 17 calculates an average value of the brightness-level values at a depth range 7c corresponding to the region of interest 6b, for each of the scanning lines 6c, 6d, and 6e. Subsequently, the controlling unit 17 judges whether each of the calculated average values is equal to or larger than the first threshold value. The first threshold value is set by the operator in advance to a value that cannot be exceeded if the ultrasound probe 1 is positioned away from the patient P. For example, the first threshold value is set on the basis of the white noise level. If all the average values calculated for the scanning lines 6c, 6d, and 6e are equal to or larger than the first threshold value, the controlling unit 17 permits push pulses to be transmitted, because the controlling unit 17 determines that the ultrasound probe 1 is not positioned away from the patient P. On the contrary, if one or more of the average values are smaller than the first threshold value, the controlling unit 17 does not permit push pulses to be transmitted, because the controlling unit 17 determines that at least a part of the surface of the probe is positioned away from the patient P. More specifically, if the average value of the brightness-levels calculated with respect to the scanning line 6d is smaller than the first threshold value, the controlling unit 17 determines that a part of the probe surface corresponding to the scanning line 6d is positioned away from the patient P. The first threshold value used in this situation is a threshold value for the brightness-level values and is different from a threshold value for the strength of the reflected-wave signals. Further, the controlling unit 17 does not necessarily have to make judgments about the plurality of scanning lines. For example, it is acceptable for the controlling unit 17 to make a judgment only about the scanning line 6c. Further, the controlling unit 17 does not necessarily have to make a judgment about the depth range 7c. For example, it is acceptable for the controlling unit 17 to determine that the ultrasound probe 1 is not positioned away from the patient P, if the brightness-level values in the range 7a are smaller than a predetermined threshold value.

Further, by using the strength of the received reflected-wave signals, the controlling unit 17 performs a process of judging whether any contrast agent is present in the body of the patient P, so as to address the issue of an impact on tissues in the patient's body that may be made via a contrast agent, if a contrast agent is being used. For example, if the strength of the reflected-wave signals in a predetermined second depth range is lower than a second threshold value, the controlling unit 17 permits push pulses to be transmitted. On the contrary, if the strength of the reflected-wave signals in the predetermined second depth range is equal to or higher than the second threshold value, the controlling unit 17 does not permit push pulses to be transmitted.

Figure 8:
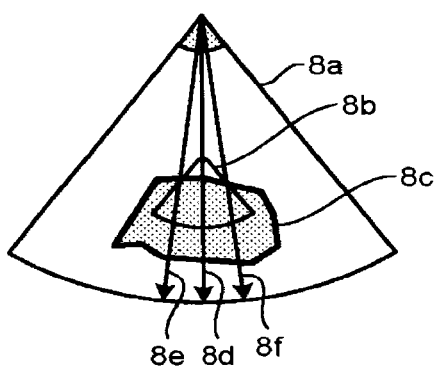
FIG. 8 is a third drawing for explaining another process performed by the controlling unit.
Figure 9:
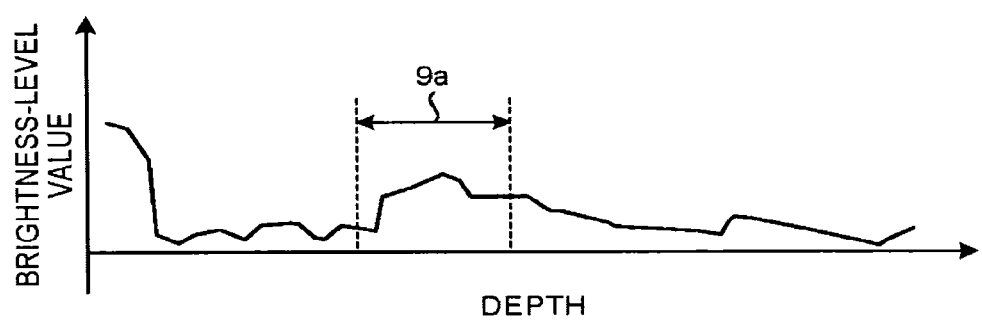
FIG. 9 is a fourth drawing for explaining said another process performed by the controlling unit.

Next, the process performed by the controlling unit 17 to judge whether any contrast agent is present in the body of the patient P will be explained with reference to FIGS. 8 and 9. FIGS. 8 and 9 are drawings for explaining a process performed by the controlling unit 17. FIG. 8 illustrates an example of an ultrasound image 8a generated in a B-mode. In the ultrasound image 8a, a region of interest 8b serving as a processing target has been set in advance by the operator of the ultrasound diagnosis apparatus. FIG. 8 illustrates an example in which a contrast agent is present in a region 8c of the ultrasound image 8a.

FIG. 9 illustrates an example of brightness-level values on a scanning line 8d that passes through the region of interest 8b. In FIG. 9, the vertical axis expresses the brightness-level value of the ultrasound image 8a, whereas the horizontal axis expresses the depth of the ultrasound image 8a. As illustrated in FIG. 9, while the ultrasound probe 1 is in contact with the patient P, reflections between the lens surface and the transducer elements converge in a shorter period of time than in the example illustrated in FIG. 7, so that reflected-wave signals corresponding to the depths are received. From each of a scanning lines 8e and 8f, brightness-level values are obtained in a manner similar to those from the scanning line 8d. In the present example, the situation where the controlling unit 17 makes the judgment by using the brightness-level values is explained, because the explanation is based on an association between the ultrasound image and the scanning lines; however, it should be noted that the brightness-level values correspond to the strengths of the reflected-wave signals. In other words, the controlling unit 17 is able to judge whether any contrast agent is present in the body of the patient P by using either the strength of the reflected-wave signals or the brightness-level values. When the strength of the reflected-wave signals is being used, the depth direction is expressed by time, and not by the distance.

For example, the controlling unit 17 calculates an average value of the brightness-level values at a depth range 9a corresponding to the region of interest 8b, for each of the scanning lines 8d, 8e, and 8f. Subsequently, the controlling unit 17 judges whether each of the calculated average values is smaller than the second threshold value. The second threshold value is set by the operator in advance to a value that is exceeded if a contrast agent is present in the body of the patient P. For example, the second threshold value is set on the basis of the type of the contrast agent, a transmission/reception condition of the B-mode pulses, or the diagnosed site. If all the average values calculated for the scanning lines 8d, 8e, and 8f are smaller than the second threshold value, the controlling unit 17 permits push pulses to be transmitted, because the controlling unit 17 determines that no contrast agent is present in the body of the patient P. On the contrary, if one or more of the average values are equal to or larger than the second threshold value, the controlling unit 17 does not permit push pulses to be transmitted, because the controlling unit 17 determines that a contrast agent is present in at least a part of the inside of the body of the patient P. More specifically, if the average value of the brightness-levels calculated with respect to the scanning line 8d is equal to or larger than the second threshold value, the controlling unit 17 determines that a contrast agent is present in a site corresponding to the scanning line 8d. The second threshold value used in this situation is a threshold value for the brightness-level values and is different from a threshold value for the strength of the reflected-wave signals.

When the controlling unit 17 permits push pulses to be transmitted, the controlling unit 17 stops the B-mode pulses that are transmitted/received in the elastography mode. Further, the controlling unit 17 causes the transmitting and receiving unit 11 to transmit the push pulses. Subsequently, the controlling unit 17 causes the propagation speed of the shear wave to be measured. After that, the controlling unit 17 generates firmness image data, on the basis of the measured propagation speed. Subsequently, the controlling unit 17 causes the monitor 2 to display the generated firmness image data. After that, the controlling unit 17 resumes the transmission/reception of the B-mode pulses. On the contrary, when the controlling unit 17 does not permit push pulses to be transmitted, the controlling unit 17 causes the monitor 2 to display a message indicating that the transmission of push pulses is not permitted. In that situation, the transmission/reception of the B-mode pulses is continued. Further, the controlling unit 17 may provide information by using an acoustic signal representing a buzzer or speech.

The message indicating that the transmission of push pulses is not permitted may be displayed as mutually-different messages, for example, between when a judgment is made on whether the ultrasound probe 1 is positioned away from the patient P and when a judgment is made on whether any contrast agent is present in the body of the patient P. In other words, in the former situation, if the strength of the reflected-wave signals in the predetermined first depth range is lower than the first threshold value, the controlling unit 17 causes a message to be displayed indicating that a part or the entirety of the surface of the ultrasound probe 1 is positioned away from the patient P. More specifically, the controlling unit 17 causes the monitor 2 to display a message such as "the probe is positioned away from the patient". In contrast, in the latter situation, if the strength of the reflected-wave signals in the predetermined second depth range is equal to or higher than the second threshold value, the controlling unit 17 causes a message to be displayed indicating that a contrast agent is present in the body of the patient P. More specifically, the controlling unit 17 causes the monitor 2 to display a message such as "a contrast agent is remaining in the body of the patient".

As explained above, the controlling unit 17 controls the transmission of the push pulses in accordance with the strength of the reflected-wave signals of the B-mode pulses.

Figure 10:
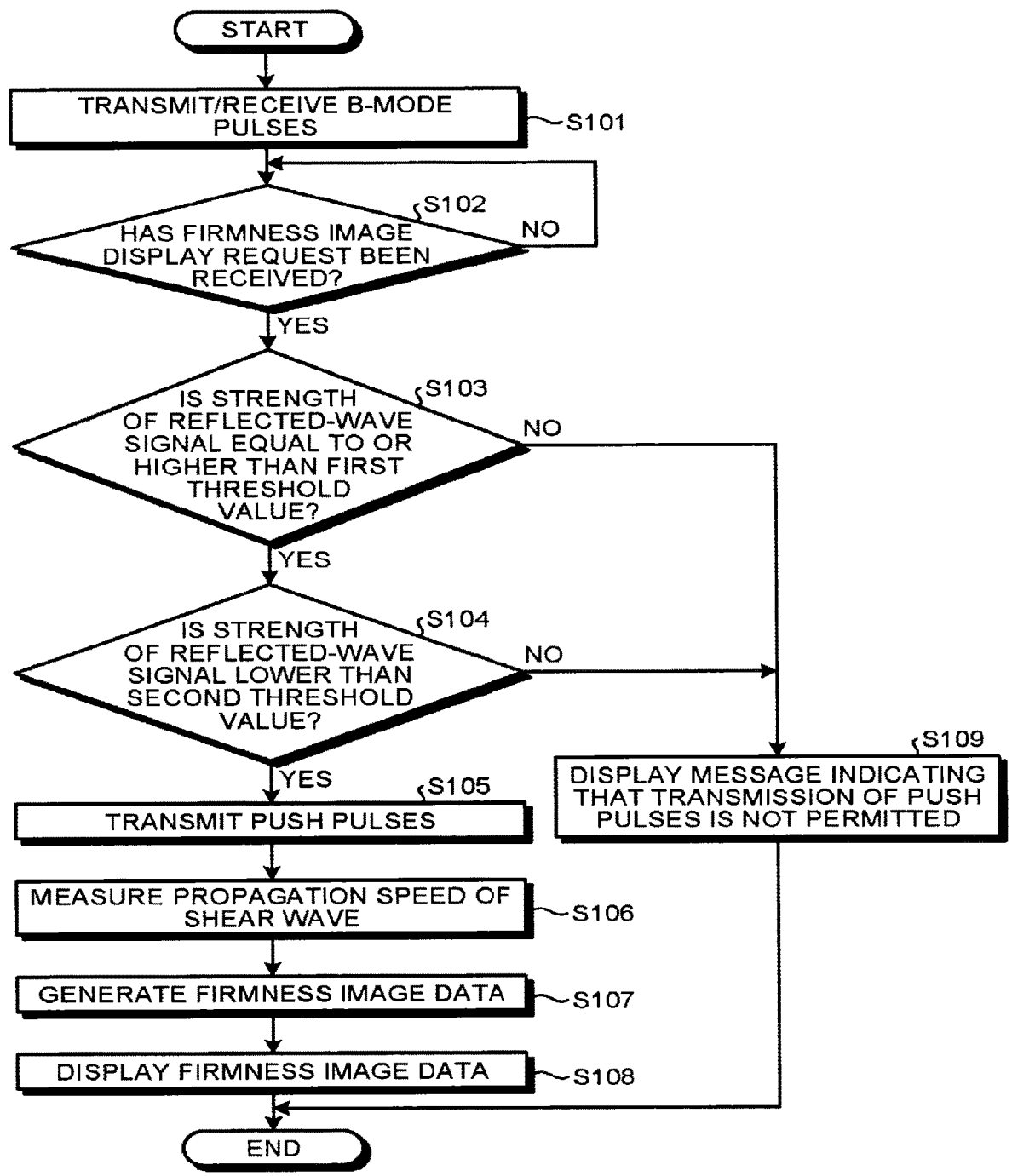
FIG. 10 is a flowchart for explaining an exemplary processing procedure performed by the ultrasound diagnosis apparatus according to the first embodiment.

Next, a processing procedure performed by the ultrasound diagnosis apparatus according to the first embodiment will be explained with reference to FIG. 10. FIG. 10 is a flowchart for explaining an exemplary processing procedure performed by the ultrasound diagnosis apparatus according to the first embodiment. FIG. 10 illustrates, as an example, a processing procedure performed in an elastography mode. In other words, the processing procedure illustrated in FIG. 10 corresponds to a processing procedure performed after the operator has switched the operation mode into the elastography mode. Further, in the present example, a situation will be explained where the controlling unit 17 performs the process by using the strength of the reflected-wave signals, and not the brightness-level values.

As illustrated in FIG. 10, in the elastography mode, the controlling unit 17 causes the transmitting and receiving unit 11 to transmit/receive B-mode pulses so as to cause the monitor 2 to display a B-mode image in a substantially real-time manner (step S101). After that, the input unit 3 receives an input of a firmness image display request (step S102). It should be noted that, until the input unit 3 receives an input of a firmness image display request (step S102: No), the controlling unit 17 causes the B-mode image to be displayed in a substantially real-time manner and does not perform the processes at step S103 and thereafter.

When the input unit 3 has received the input of the firmness image display request (step S102: Yes), the controlling unit 17 judges, for example, whether the strength of the reflected-wave signal of the B-mode pulse that was received immediately prior is equal to or higher than the first threshold value (step S103). The controlling unit 17 thus checks to see if the ultrasound probe 1 is not positioned away from the patient P. For example, the controlling unit 17 judges whether the strength of the reflected-wave signal in the predetermined first depth range is equal to or higher than the first threshold value, for each of a plurality of scanning lines. If the strength of the reflected-wave signal in the predetermined first depth range is equal to or higher than the first threshold value for all of the scanning lines serving as the judgment targets, the controlling unit 17 determines that the ultrasound probe 1 is not positioned away from the patient P (step S103: Yes). On the contrary, if the strength of the reflected-wave signal in the predetermined first depth range is lower than the first threshold value for one or more of the scanning lines, the controlling unit 17 determines that at least a part of the ultrasound probe 1 is positioned away from the patient P (step S103: No).

If the strength of the reflected-wave signal is equal to or higher than the first threshold value (step S103: Yes), the controlling unit 17 judges whether the strength of the reflected-wave signal is lower than the second threshold value (step S104). The controlling unit 17 thereby judges whether any contrast agent is present in the body of the patient P. For example, the controlling unit 17 judges whether the strength of the reflected-wave signal in the predetermined second depth range is lower than the second threshold value, for each of a plurality of scanning lines. If the strength of the reflected-wave signal in the predetermined second depth range is lower than the second threshold value for all of the scanning lines serving as the judgment targets, the controlling unit 17 determines that no contrast agent is present in the site corresponding to the predetermined second depth range (step S104: Yes). On the contrary, if the strength of the reflected-wave signal in the predetermined second depth range is equal to or higher than the second threshold value for one or more of the scanning lines, the controlling unit 17 determines that a contrast agent is present in the site corresponding to the predetermined second depth range (step S104: No).

If the strength of the reflected-wave signal is lower than the second threshold value (step S104: Yes), the controlling unit 17 causes the transmitting and receiving unit 11 to stop the transmission/reception of the B-mode pulses and to transmit push pulses (step S105). Subsequently, the controlling unit 17 causes the B-mode processing unit 12 to measure the propagation speed of the shear wave (step S106). After that, the controlling unit 17 generates firmness image data on the basis of the measured propagation speed (step S107). Subsequently, the controlling unit 17 causes the monitor 2 to display the generated firmness image data (step S108). After that, the controlling unit 17 resumes the transmission/reception of the stopped B-mode pulses and causes a B-mode image to be displayed in a substantially real-time manner.

On the contrary, if the strength of the reflected-wave signal is lower than the first threshold value (step S103: No), the controlling unit 17 causes the monitor 2 to display a message indicating that the transmission of push pulses is not permitted (step S109). Further, if the strength of the reflected-wave signal is equal to or higher than the second threshold value (step S104: No), the controlling unit 17 proceeds to the process at step S109.

In this situation, for example, the processes at steps S103 and S104 do not necessarily have to be performed according to the processing procedure described above. It is acceptable to perform the process at step S103 after performing the process at step S104.

Further, for example, both of the processes at steps S103 and S104 do not necessarily have to be performed. In other words, it is acceptable to perform only one of the processes at step S103 and step S104.

Further, for example, if the judgment result at step S103 is in the negative, the controlling unit 17 may cause the monitor 2 to display a message such as "the probe is positioned away from the patient" at step S109. Further, if the judgment result at step S104 is in the negative, the controlling unit 17 may cause the monitor 2 to display a message such as "a contrast agent is remaining in the body of the patient" at step S109.

FIG. 10 illustrates the example in which the controlling unit 17 performs the judging process by using the strength of the reflected-wave signal of the B-mode pulse that was transmitted/received immediately prior to the input of the firmness image display request; however, possible embodiments are not limited to this example. For instance, the controlling unit 17 may use the strength of the reflected-wave signal of a B-mode pulse of which the transmission/reception precedes an input of a firmness image display request by a predetermined time period. In another example, after an input of a firmness image display request has been received, the controlling unit 17 may cause a judgment-purpose B-mode pulse to be transmitted/received once, so as to perform the judging process by using the strength of the reflected-wave signal thereof.

As explained above, the ultrasound diagnosis apparatus according to the first embodiment receives the input of the firmness image display request to change the shape of the tissue in the body of the patient. When having received the input of the firmness image display request, the ultrasound diagnosis apparatus according to the first embodiment controls the transmission of the push pulses, in accordance with the strength of the B-mode pulses.

For example, when having determined that the ultrasound probe 1 is positioned away from the patient P, the ultrasound diagnosis apparatus according to the first embodiment does not permit push pulses to be transmitted. Thus, the ultrasound diagnosis apparatus according to the first embodiment is able to address the issue of an increase in the temperature at the surface of the ultrasound probe 1.

Further, when having determined that a contrast agent is present in the body of the patient P, the ultrasound diagnosis apparatus according to the first embodiment does not permit push pulses to be transmitted. Thus, the ultrasound diagnosis apparatus according to the first embodiment is also able to address the issue of an impact on the tissues in the patient's body that may be made via the contrast agent.

As a result, the ultrasound diagnosis apparatus according to the first embodiment is able to safely use the ultrasound waves that are transmitted for the purpose of changing the shape of the tissue in the body of the patient.

Second Embodiment

The first embodiment above is explained using the example where no push pulse is transmitted if it has been determined that a contrast agent is present in the body of the patient P; however, possible embodiments are not limited to this example. For instance, the ultrasound diagnosis apparatus may also leave the decision on whether push pulses should be transmitted or not to the operator. Accordingly, in a second embodiment, a process that is performed when the decision on whether push pulses should be transmitted or not is left to the operator will be explained. All of the other functional configurations explained in the first embodiment are applied to the ultrasound diagnosis apparatus according to the second embodiment, except for the process that is performed to leave the decision on whether push pulses should be transmitted or not to the operator.

Figure 11:
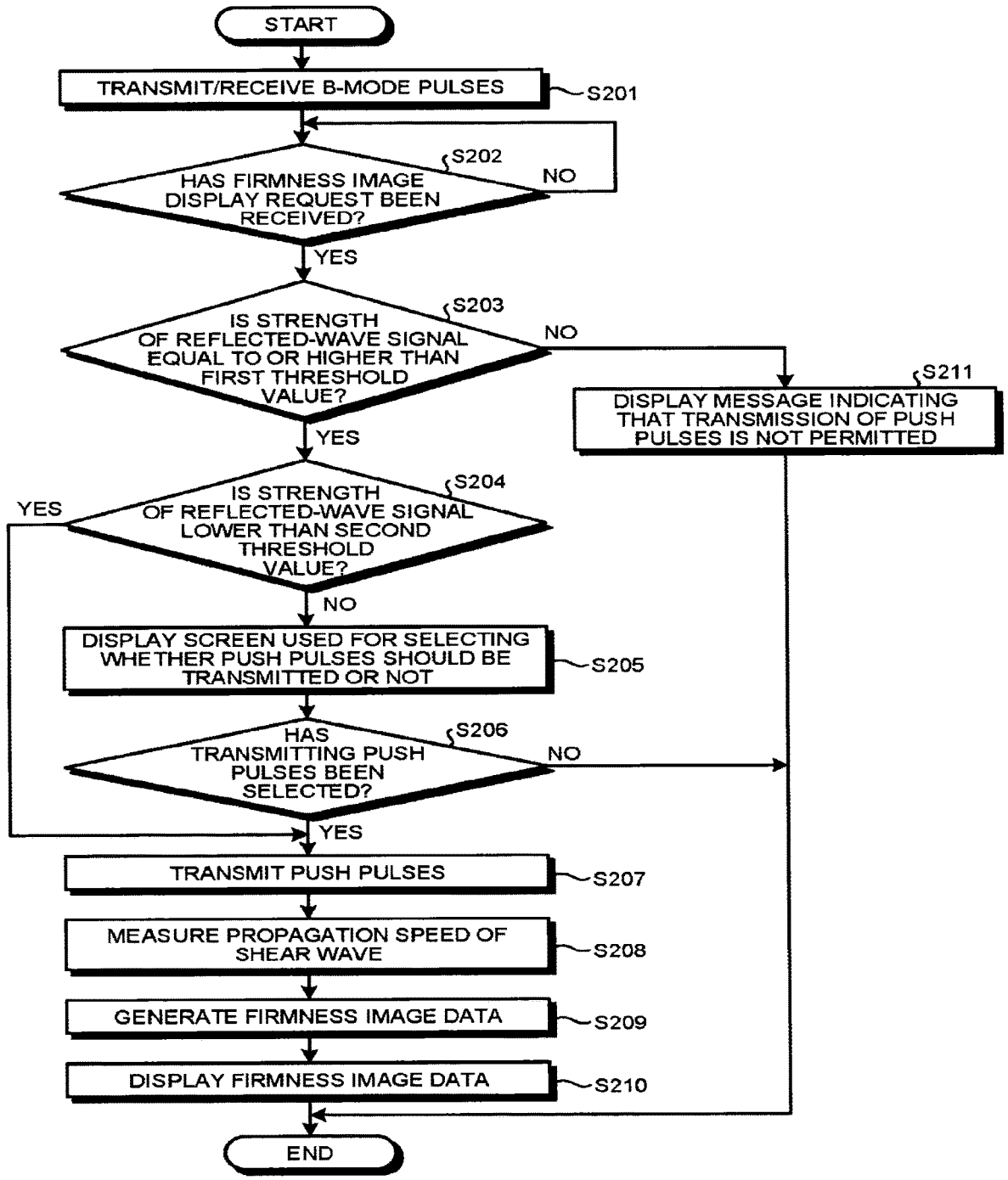
FIG. 11 is a flowchart for explaining an exemplary processing procedure performed by an ultrasound diagnosis apparatus according to a second embodiment.

FIG. 11 is a flowchart for explaining an exemplary processing procedure performed by the ultrasound diagnosis apparatus according to the second embodiment. As illustrated in FIG. 11, in the elastography mode, the controlling unit 17 causes the transmitting and receiving unit 11 to transmit/receive B-mode pulses so as to cause the monitor 2 to display a B-mode image in a substantially real-time manner (step S201). After that, the input unit 3 receives an input of a firmness image display request (step S202). It should be noted that, until the input unit 3 receives an input of a firmness image display request (step S202: No), the controlling unit 17 causes the B-mode image to be displayed in a substantially real-time manner and does not perform the processes at step S203 and thereafter.

When the input unit 3 has received the input of the firmness image display request (step S202: Yes), the controlling unit 17 judges, for example, whether the strength of the reflected-wave signal of the B-mode pulse that was received immediately prior is equal to or higher than the first threshold value (step S203). The controlling unit 17 thus checks to see if the ultrasound probe 1 is not positioned away from the patient P.

If the strength of the reflected-wave signal is equal to or higher than the first threshold value (step S203: Yes), the controlling unit 17 judges whether the strength of the reflected-wave signal is lower than the second threshold value (step S204). The controlling unit 17 thus judges whether any contrast agent is present in the body of the patient P.

If the strength of the reflected-wave signal is equal to or higher than the second threshold value (step S204: No), the controlling unit 17 causes the monitor 2 to display a screen used for selecting whether push pulses should be transmitted or not (step S205). If transmitting push pulses has been selected (step S206: Yes), the controlling unit 17 causes the transmitting and receiving unit 11 to stop the transmission/reception of the B-mode pulses and to transmit push pulses (step S207). Subsequently, the controlling unit 17 causes the B-mode processing unit 12 to measure the propagation speed of the shear wave (step S208). After that, the controlling unit 17 generates firmness image data on the basis of the measured propagation speed (step S209). Subsequently, the controlling unit 17 causes the monitor 2 to display the generated firmness image data (step S210). After that, the controlling unit 17 resumes the transmission/reception of the stopped B-mode pulses and causes a B-mode image to be displayed in a substantially real-time manner.

On the contrary, if transmitting push pulses has not been selected (step S206: No), the controlling unit 17 ends the process without causing any push pulse to be transmitted.

Further, if the strength of the reflected-wave signal is lower than the second threshold value (step S204: Yes), the controlling unit 17 proceeds to the process at step S207.

Further, if the strength of the reflected-wave signal is lower than the first threshold value (step S203: No), the controlling unit 17 causes the monitor 2 to display a message indicating that the transmission of push pulses is not permitted (step S211). The controlling unit 17 may provide the message by using an acoustic signal representing a buzzer or speech.

In this situation, the processes at steps S203 and S211 do not necessarily have to be performed. In other words, it is acceptable to perform the process at step S204, after performing the process at step S202. Further, in the present example, the situation was explained in which the controlling unit 17 performs the judging process by using the strength of the reflected-wave signal of the B-mode pulse that was transmitted/received immediately prior to the input of the firmness image display request; however, possible embodiments are not limited to this example.

As explained above, when it has been determined that a contrast agent is present in the body of the patient P, the ultrasound diagnosis apparatus according to the second embodiment is able to leave the decision on whether push pulses should be transmitted or not to the operator. In other words, the ultrasound diagnosis apparatus according to the second embodiment is configured so that, even when it has been determined that a contrast agent is present in the body of the patient P, it is possible to transmit the push pulses according to the operator's judgment.

The ultrasound diagnosis apparatus according to the second embodiment is also configured so as to be able to purposefully transmit an ultrasound wave under a predetermined condition. Examples of ultrasound waves that are purposefully transmitted under the predetermined condition include an ultrasound wave for the use in a Drug Delivery System (DDS) (hereinafter a "DDS ultrasound wave"). Next, an example will be explained in which the ultrasound diagnosis apparatus according to the second embodiment is applied to a DDS that employs ultrasound waves (hereinafter, an "ultrasound DDS").

First, the ultrasound DDS will be briefly explained. Generally speaking, an ultrasound DDS may be configured so that microbubbles enclosing a drug therein (hereinafter, "drug bubbles") are administered to a patient, and at the point in time when the drug bubbles have reached a predetermined site, the drug bubbles are destructed by emitting an ultrasound wave from the outside of the body of the patient, so that the enclosed drug is released on the inside of the patient. In this situation, because the drug bubbles contain microbubbles like contrast agents do, a powerful reflected-wave signal is obtained in accordance with the quantity of drug bubbles that are present in the body.

Accordingly, the ultrasound diagnosis apparatus according to the second embodiment is used for transmitting a DDS ultrasound wave that destructs drug bubbles administered to a patient. More specifically, in the ultrasound diagnosis apparatus according to the second embodiment, the controlling unit 17 receives an input of a request indicating that a DDS ultrasound wave should be transmitted. After that, the controlling unit 17 causes B-mode pulses to be transmitted/received. If the strength of the reflected-wave signals of the B-mode pulses in the predetermined second depth range is equal to or higher than a second threshold value, the controlling unit 17 causes the monitor 2 to display a screen used for selecting whether a DDS ultrasound wave should be transmitted or not. Subsequently, if transmitting a DDS ultrasound wave has been selected, the controlling unit 17 causes the transmitting and receiving unit 11 to transmit a DDS ultrasound wave. In this situation, the second threshold value is set in accordance with, for example, the amount of drug to be released on the inside of the patient, i.e., the quantity of the drug bubbles that have reached the predetermined site.

As explained above, by using the ultrasound diagnosis apparatus according to the second embodiment, the operator is able to cause the DDS ultrasound wave to be transmitted at the stage when the drug bubbles have sufficiently reached the predetermined site.

Third Embodiment

In the first and the second embodiments described above, the example is explained in which the transmission of the push pulses is controlled by using the brightness-level values of the B-mode image that is displayed before the firmness image is displayed or by using the strength of the reflected-wave signals of the B-mode pulses that are transmitted/received for the purpose of displaying the B-mode image; however, possible embodiments are not limited to this example. For instance, the ultrasound diagnosis apparatus may control the transmission of the push pulses by performing a judging process with the use of a judgment-purpose pulse that is different from the B-mode pulses and is for the purpose of performing the judging process. Thus, as a third embodiment, a process that is performed by the ultrasound diagnosis apparatus to control the transmission of the push pulses by using the judgment-purpose pulse, in place of the B-mode pulses, will be explained.

Figure 12:
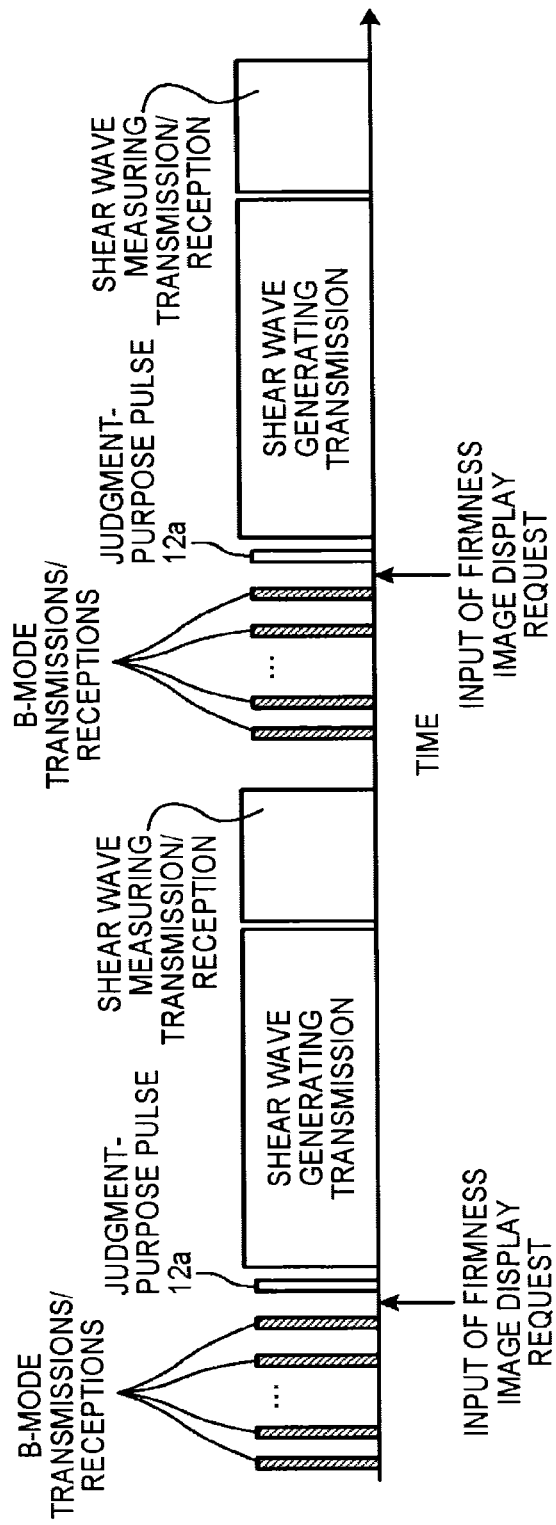
FIG. 12 is a drawing for explaining a workflow in an elastography procedure according to a third embodiment.

FIG. 12 is a drawing for explaining a workflow in an elastography procedure according to the third embodiment. The workflow illustrated in FIG. 12 is different from the workflow illustrated in FIG. 5 because a judgment-purpose pulse 12a is transmitted/received after an input of a firmness image display request is received.

More specifically, as illustrated in FIG. 12, when the input unit 3 has received an input of a firmness image display request, the controlling unit 17 causes the transmitting and receiving unit 11 to transmit/receive the judgment-purpose pulse 12a. After that, the controlling unit 17 controls the transmission of the push pulses, in accordance with the strength of the reflected-wave signal of the received judgment-purpose pulse 12a. More specifically, by using the strength of the received reflected-wave signal, the controlling unit 17 performs the process of judging whether the ultrasound probe 1 is positioned away from the patient P and performs the process of judging whether any contrast agent is present in the body of the patient P.

The judgment-purpose pulse that is transmitted/received in the example illustrated in FIG. 12 is an ultrasound wave transmitted/received for the purpose of performing the judging process explained in the first and the second embodiments and is therefore not used in the imaging process. For this reason, for example, the judgment-purpose pulse may be transmitted/received with respect to all the scanning lines in the scanned region or may be transmitted/received with respect to only one or more arbitrary scanning lines. Further, the strength of the judgment-purpose pulse and other scan conditions may be the same as those of the B-mode pulses or may be different from those of the B-mode pulses. Furthermore, the judgment-purpose pulse is an example of an ultrasound wave that is transmitted with timing different from that of the push pulses.

As explained above, the ultrasound diagnosis apparatus according to the third embodiment controls the transmission of the push pulses by using the judgment-purpose pulse, in place of the B-mode pulses. As a result, the ultrasound diagnosis apparatus according to the third embodiment is able to safely use the ultrasound waves transmitted for the purpose of changing the shape of a tissue in the body of the patient, without the need to necessarily generate a B-mode image.

The judgment-purpose pulse explained in the third embodiment does not necessarily have to be transmitted/received after a firmness image display request has been input. In another example, judgment-purpose pulses may be transmitted/received regularly.

FIG. 13 is a drawing for explaining a modification example of the workflow in the elastography procedure according to the third embodiment. The workflow illustrated in FIG. 13 is different from the workflow illustrated in FIG. 12 because judgment-purpose pulses 13a are transmitted/received regularly.

More specifically, as illustrated in FIG. 13, in a mode in which it is possible to display a firmness image by implementing elastography, the judgment-purpose pulses 13a are transmitted/received regularly with timing different from that of the B-mode pulses. Even more specifically, the controlling unit 17 causes the judgment-purpose pulses 13a to be transmitted/received periodically with arbitrary timing, so that each of the judgment-purpose pulses 13a is appropriately inserted between B-mode pulses that are repeatedly transmitted/received. Further, when the input unit 3 has received an input of a firmness image display request, the controlling unit 17 controls the transmission of the push pulses in accordance with, for example, the strength of the reflected-wave signal of the judgment-purpose pulse 13a that was transmitted/received immediately prior to the input of the firmness image display request. More specifically, by using the strength of the received reflected-wave signal, the controlling unit 17 performs the process of judging whether the ultrasound probe 1 is positioned away from the patient P and performs the process of judging whether any contrast agent is present in the body of the patient P. Alternatively, the controlling unit 17 may use the strength of the reflected-wave signal of a judgment-purpose pulse 13a that was transmitted/received a number of seconds before a firmness image display request is input. In other words, the controlling unit 17 controls the transmission of the push pulses by using the strength of the reflected-wave signal of any one of the plurality of judgment-purpose pulses 13a transmitted/received regularly.

Other Configurations

The respective components in the respective apparatuses shown in the explanation of the first to the third embodiments are of functional concept, and it is not necessarily required to be physically configured as shown in the drawings. Specifically, a specific form of distribution and integration of the respective devices are not limited to the ones shown in the drawings, and it can be configured such that all or a part thereof is functionally or physically distributed or integrated in arbitrary units according to various kinds of load and usage condition and the like. Furthermore, as for the respective processing functions of the respective devices, all or an arbitrary part thereof can be implemented by a central processing unit (CPU) and a computer program that is analyzed and executed by the CPU, or can be implemented as hardware by wired logic.

For example, the ultrasound diagnosis apparatus shown in FIG. 1 may be configured as shown in FIG. 14. FIG. 14 is a block diagram of an exemplary configuration of an ultrasound diagnosis apparatus according to other embodiments.

As illustrated in FIG. 14, an ultrasound diagnosis apparatus includes an ultrasound probe 101, a display 102, input circuitry 103, and an apparatus main body 110. The ultrasound probe 101, the display 102, the input circuitry 103, and the apparatus main body 110 correspond to the ultrasound probe 1, the monitor 2, the input unit 3, and the apparatus main body 10 shown in FIG. 1, respectively. The input circuitry 103 is an example of input circuitry in the accompanying claims.

The apparatus main body 110 includes transmitting and receiving circuitry 111, B-mode processing circuitry 112, Doppler processing circuitry 113, image generating circuitry 114, memory circuitry 115, and processing circuitry 116. The transmitting and the receiving circuitry 111, the B-mode processing circuitry 112, the Doppler processing circuitry 113, the image generating circuitry 114, and the processing circuitry 116 correspond to the transmitting and receiving unit 11, the B-mode processing unit 12, the Doppler processing unit 13, the image generating unit 14, and the controlling unit 17 shown in FIG. 1, respectively. The memory circuitry 115 correspond to the image memory 15 and the internal storage unit 16 shown in FIG. 1. The processing circuitry 116 is an example of processing circuitry in the accompanying claims.

The processing circuitry 116 performs a controlling function that the controlling unit 17 performs. For example, each of the respective processing functions performed by the processing circuitry 116, is stored in the memory circuitry 115 in a form of a computer-executable program. The processing circuitry 116 is a processor that loads programs from the memory circuitry 115 and executes the programs so as to implement the respective functions corresponding to the programs. In other words, the processing circuitry 116 that has loaded the programs has the controlling function. That is, the processing circuitry 116 loads a program corresponding to the controlling function from the memory circuitry 115 and executes the program so as to perform the same processing as that of the controlling unit 17.

For example, Steps S103 to S106 illustrated in FIG. 10 is a step that is implemented by the processing circuitry 116 loading the program corresponding to the function of the controlling unit 17 from the memory circuitry 115 and executing the program.

In FIG. 14, the processing function performed by the function of the controlling unit 17 is described as being implemented in the single processing circuit. The function, however, may be implemented by configuring a processing circuit by combining a plurality of separate processors and causing each of the processors to execute a program.

The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the present embodiment are not limited to a case in which each of the processors is configured as a single circuit. A plurality of separate circuits may be combined as one processor that implements the respective functions. Furthermore, the components illustrated in FIG. 14 may be integrated into one processor that implements the respective functions.

The respective circuitry exemplified in FIG. 14 may be distributed or integrated as appropriate. For example, the processing circuitry 116 and the image generating circuitry 114 may be integrated.

The image processing method explained in any of the first to the third embodiments described above may be realized by causing a computer such as a personal computer or a workstation to execute an image processing computer program (hereinafter, an "image processing program") that is prepared in advance. The image processing program may be distributed via a network such as the Internet. Further, it is also possible to record the image processing program onto a computer-readable non-transitory recording medium such as a hard disk, a flexible disk (FD), a Compact Disk Read-Only Memory (CD-ROM), a Magneto-optical (MO) disk, a Digital Versatile Disk (DVD), or a flash memory such as a Universal Serial Bus (USB) memory or a Secure Digital (SD) card memory, so that a computer is able to read the image processing program from the non-transitory recording medium and to execute the read image processing program.

In the first to the third embodiments described above, the example is explained in which the ultrasound diagnosis apparatus controls the transmission of the push pulses; however, possible embodiments are not limited to this example. For instance, the first and the second embodiments are similarly applicable not only to the push pulses, but also to any other situations that use an ultrasound wave transmitted for the purpose of changing the shape of a tissue in the body of a patient, such as an ultrasound wave used in a DDS or an ultrasound wave used for hemostasis.

According to at least one aspect of the exemplary embodiments described above, it is possible to safely use the ultrasound waves that are transmitted for the purpose of changing the shape of a tissue in the body of a patient.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
transmitting and receiving circuitry configured to control an ultrasound probe to transmit a push pulse to generate a shear wave for elastography and control the ultrasound probe to transmit/receive a shear wave measuring pulse that is transmitted/received with timing different from that of the push pulse and has a power different from that of the push pulse;
input circuitry configured to receive an input of a request indicating that the push pulse should be transmitted; and
processing circuitry configured to
estimate a tumor site using an administered contrast agent,
detect a presence of the administered contrast agent in a body of a patient by determining whether a strength of a reflected-wave signal of the shear wave measuring pulse or at least one pixel value of an image resulting from an imaging process performed by using the reflected-wave signal of the shear wave measuring pulse in a predetermined first depth range in the body of the patient after the input circuitry has received the input of the request is lower than a first threshold value indicating the presence of the administered contrast agent,
permit the push pulse to be transmitted when the presence of the administered contrast agent is not detected, and
block the push pulse from being transmitted when the presence of the administered contrast agent is detected.

2. The ultrasound diagnosis apparatus according to claim 1, wherein the processing circuitry is further configured to permit the push pulse to be transmitted, when determining that the strength of the reflected-wave signal in a predetermined second depth range is equal to or higher than a second threshold value, and
the processing circuitry is further configured to block the push pulse from being transmitted, when determining that the strength of the reflected-wave signal in the predetermined second depth range is lower than the second threshold value, the second threshold value being set to a value that cannot be exceeded when an ultrasound probe is positioned away from the patient.

3. The ultrasound diagnosis apparatus according to claim 1, wherein the processing circuitry is further configured to output information indicating that the transmission of the push pulse is blocked, in response to the processing circuitry blocking the push pulse from being transmitted.

4. The ultrasound diagnosis apparatus according to claim 1, wherein the processing circuitry is further configured to cause a predetermined display to perform the following function in response to the processing circuitry blocking the push pulse from being transmitted: display a screen used for selecting whether or not the push pulse should be transmitted.

5. The ultrasound diagnosis apparatus according to claim 1, wherein the processing circuitry is further configured to cause the transmitting and receiving circuitry to perform the following functions in response to the input circuitry receiving the input of the request:
- control the ultrasound probe to transmit the shear wave measuring pulse and
- control the ultrasound probe to transmit the push pulse in accordance with the strength of the reflected-wave signal of the shear wave measuring pulse or the at least one pixel value of the image resulting from the imaging process performed by using the shear wave measuring pulse.

6. The ultrasound diagnosis apparatus according to claim 1, wherein
- the transmitting and receiving circuitry is further configured to control the ultrasound probe to regularly transmit/receive judgment-purpose ultrasound waves that are neither used in an imaging process nor as the shear wave measuring pulse, wherein the judgement-purpose ultrasound waves have timings that are different from that of the shear wave measuring pulse used in the imaging process, and
- the processing circuitry is further configured to perform the following function in response to the input circuitry receiving the input of the request: control whether the push pulse should be transmitted or not, using a strength of one of the judgment-purpose ultrasound waves.

7. The ultrasound diagnosis apparatus according to claim 1, wherein the administered contrast agent comprises microbubbles administered to the body of the patient prior to receiving the request indicating that the push pulse should be transmitted.

8. The apparatus according to claim 1, wherein the first threshold value is set such that the strength or the at least one pixel value in the predetermined first depth range does not exceed the first threshold value at a time when the administered contrast agent is not present in the body of the patient.

* * * * *